United States Patent [19]

Jeanne et al.

[11] Patent Number: 4,801,359
[45] Date of Patent: Jan. 31, 1989

[54] SOLID COMPOSITIONS BASED ON SUPEROXIDES HAVING HIGH IONIC CONDUCTIVITY, THEIR METHOD OF MANUFACTURE, AND THEIR ELECTROCHEMICAL APPLICATIONS

[75] Inventors: Francis Jeanne, Jouy-En-Josas; Serge Lombard, Longjumeau; Emmanuel Schmidt, Issy-Les-Moulineaux, all of

[73] Assignee: L'Air Liquide, Societe Anonyme Pour L'Etude et Exploitation Des Procedes Georges Claude, Paris, France

[21] Appl. No.: 925,024
[22] PCT Filed: Feb. 10, 1986
[86] PCT No.: PCT/FR86/00035
§ 371 Date: Nov. 24, 1986
§ 102(e) Date: Nov. 24, 1986
[87] PCT Pub. No.: WO86/04932
PCT Pub. Date: Aug. 28, 1986

[30] Foreign Application Priority Data

Feb. 15, 1985 [FR] France .................. 85 02218

[51] Int. Cl.⁴ ........................ C25G 1/02
[52] U.S. Cl. ................... 204/1 T; 204/59 R; 204/129; 204/130; 204/252; 204/282; 204/283; 204/295; 204/296; 521/27; 564/291; 564/296
[58] Field of Search ............ 204/59 R, 296, 295, 204/283, 282, 252, 130, 1 T, 129; 521/27; 564/291

[56] References Cited

U.S. PATENT DOCUMENTS

Re. 28,792  4/1976  Ruka et al. .............. 204/1 T
4,167,457  9/1979  Giner ..................... 204/1 T
4,475,994  10/1984  Gagne et al. ........... 204/129
4,680,101  7/1987  Darlington et al. ...... 204/296

Primary Examiner—R. L. Andrews
Attorney, Agent, or Firm—Young & Thompson

[57] ABSTRACT

Solid compositions based on superoxides comprise a material inert with respect to $O_2{-}$ anions playing the role of matrix with regard to these anions, and $O_2{-}$ anions, these compositions forming a material stable up to about 100° C. This matrix permits the mobility of the $O_2{-}$ anions in this temperature region. These compositions are usable as electrolytes (1) in an electrochemical cell.

50 Claims, 2 Drawing Sheets

SOLID COMPOSITIONS BASED ON SUPEROXIDES HAVING HIGH IONIC CONDUCTIVITY, THEIR METHOD OF MANUFACTURE, AND THEIR ELECTROCHEMICAL APPLICATIONS

The invention has as an object solid compositions based on superoxides having high ionic conductivity, their method of manufacture, and their electrochemical applications.

It addresses, in particular their applications as electrolytes in devices for the separation or analysis of oxygen.

Molecular oxygen $O_2$ is easily reducible to the anionic state by reason of its very electro-active character which distinguishes it from other constituents of air (nitrogen, rare gases) and numerous other gases.

The successivee anionic states of the reduction of $O_2$ lead to $O_2^-$ (superoxide ion), $O_2^{--}$ (peroxide ion) or $O_2H^-$ (hydroperoxide ion) and, with the breaking of the O—O bond, to 2 $O^{--}$ or 2 $OH^-$ (oxide and hydroxide ions respectively).

Electro-diffusion of oxygen in anionic form has already been envisioned for the separation of oxygen from a given medium.

In a general manner, a first electrode or cathode permits the reduction of the molecular oxygen to an oxygen anion which migrates through an electrolyte to a second electrode or anode where the oxide is reformed to molecular oxygen.

Several types of electrolytes have been proposed for separating out the oxygen by electro-diffusion.

The most widely used electrolytes in liquid phase are constituted by aqueous solutions of potassium hydroxide and in solid phase by zirconia doped with oxides such as those of yttrium $Y_2O_3$ or calcium CaO. The oxygen anions involved correspond respectively to the hydroxide ion $OH^-$ and the oxide ion $O^{--}$.

In these two cases, the molecular oxygen undergoes a reduction by four electrons per molecule and the oxygen molecule is severed.

The very great overvoltages arising from the need to activate the aggregate of chemical and electrochemical reactions at the electrodes entails an energy consumption much higher than the theoretical energy for separation of the oxygen.

For example, in the case of an extractor of oxygen by electro-diffusion in a potassium hydroxide solution, the voltage to be applied for producing oxygen at one bar from atmospheric air and the corresponding consumption of energy are about 100 times the minimal value given by the thermodynamics.

In the case of the zirconia that has very low conductivity at ambient temperature, it is necessary to heat above 600° C. to obtain a sufficient ionic conductivity and to activate the electrode reactions. The use of high temperatures entails moreover, problems of chemical reactivity in gaseous phase and problems of corrosion of the electrode materials.

Other media have been envisioned but have not been able to be developed such as the molten salts based on alkali nitrates functioning at temperatures of about 250° C. In this case, the corrosion of the electrodes and the precipitation of peroxides have prevented the application of these media to the production of oxygen. Moreover, in an application as a gauge of the partial pressure of oxygen, these media have response times on the order of several hours, thus rendering them unusable in practice.

The separation of gases, and in particular, the extraction of oxygen from the air are processes generally costly in energy. The processes of electro-diffusion mentioned above are particularly so because of the great overvoltages of the electrodes and also because of the significant quantities of current required, being 4 faradays per mole of oxygen transported.

Although significant efforts to reduce the over-voltages have been undertaken in the field of oxygen electrodes for fuel cells and in the field of oxygen anodes for the electrolysis of water, the solutions most frequently proposed resort to an electrocatalysis using costly compounds based on precious metals and/or organic molecules of delicate synthesis.

Furthermore, the high intensities of current necessary when the transport of one mole of oxygen involves 4 faradays entail losses of energy by the Joule effect both in the electrolytic medium and in the conductors.

U.S. Pat. No. 4,475,994 proposes an electrochemical method for separation of oxygen from the air or a mixture of gases, using an electrochemical cell comprising a cathode where the oxygen is reduced to superoxide ion $O_2^-$ and an anode where the $O_2^-$ ion is reoxidized to $O_2$, the transport of the superoxide ion being assured by an electrolyte. In this cell, the oxidation-reduction reaction involves only a single electron per $O_2$ molecule.

Nevertheless, in this case, the superoxide anion produced electrochemically at the cathode exists only transitorily, during the time of its transport to the anode where it is reoxidized: thus, unless a potential is applied, the concentration of $O_2^-$ is practically zero.

The $O_2^-$ concentration during operation of this cell has proved insufficient, for example, for a satisfactory oxygen production, from a given medium contained by it.

The work done by the applicant has shown that by using compositions of appropriate superoxides, it is possible to obtain an $O_2^-$ concentration favoring the oxidation-reduction reaction of the oxygen, and, consequently, the production of oxygen.

The invention thus has as an object to furnish new superoxide compositions with high $O_2^-$ conductivity.

It also seeks to furnish a process for preparation of these compositions and superoxide salts that is easily practiced.

The invention also has as an object to provide electrolytes based on superoxide compositions assuring the stability and the mobility of $O_2^-$ ions, as well as electrochemical apparatus containing such electrolytes, usable particularly for the separation of oxygen from the air and the production of oxygen.

The solid compositions based on superoxides of the invention are characterized in that they comprise:
a material inert with respect to superoxide anions $O_2^-$, playing the role of matrix with respect to the anions,
superoxide anions $O_2^-$,
these compositions forming a material stable up to a temperature not exceeding about 100° C., the matrix permitting the mobility of the $O_2^-$ ions in this temperature region.

As material inert with respect to the $O_2^-$ ions there is mentioned an essentially aprotic material not having any groups capable of reacting in an irreversible fashion with $O_2^-$ even under aprotic conditions, which is to say essentially: oxidizing groups, Lewis acids, electrophilic or electrodeficient centers and systems that could lead to an elimination reaction in a basic medium.

A study of these compositions shows that they possess properties of high ionic conductivity, thus rendering them particularly advantageous as materials for the elaboration of electrolytes.

They also have the advantage of assuring a satisfactory stability and mobility of the $O_2^-$ ions at moderate temperatures, in particular at temperatures on the order of ambient to about 100° C.

In the absence of any applied potential, these solid compositions contain a minimum superoxide anion $O_2^-$ concentration of at least $10^{-2}$ milliequivalents per gram, especially from 1 to 2 milliequivalents per gram.

In an advantageous manner, the compositions of the invention have filmogenic properties.

Preferred compositions occur in the form of membranes, the thickness of which is preferably less than about $500\mu$, advantageously on the order of 10 to $500\mu$, particularly about 30 to $100\mu$.

The matrix, according to a preferred embodiment of compositions of the invention, is based on a macromolecular material.

Preferably, the macromolecular material is based on a homopolymer or copolymer, cross linked as the case may be.

This polymer material, capable of assuring to the $O_2^-$ ion a satisfactory mobility for usage in electrochemistry, is more particularly constituted by a material at least partially amorphous at the temperatures of operation.

It is furthermore preferable to chose a polymer material having the highest possible dielectric constant.

Advantageously, the vitreous transition temperature $T_g$ of the phase formed by the polymer matrix containing the $O_2^-$ anions is relatively low, less than about 50° C.

More particularly, this $T_g$ is less than about 50° C. at the operating temperature.

This polymer material may be formed from a single type of polymer or from a copolymer. The polymer or the copolymer may be neutral, a superoxide salt being dissolved in the polymer matrix. Alternatively, it comprises charged sites, more particularly, a majority of cationic sites, $O_2^-$ constituting one of the counter-ions.

According to a variation, more particularly when it is desired to render a base polymer more amorphous and/or when it is desired to lower the temperature $T_g$ of the composition, the polymer material is formed from a mixture of polymers and/or copolymers.

The copolymers are block copolymers or straight chain copolymers (in which the linkage of the repeating units is regular) or also statistical copolymers in which the linkage of the repeating units is effected at random, which militates against the crystallization of the chains).

It is to be noted that each component of the mixture or copolymer may be chosen advantageously so as to improve a given quality, for example, the amorphous character, the conductivity, the dielectric constant, the hydrophobic character, the resistance to temperature, the filmogenic properties, the contact with an adjacent material.

Copolymers of this type comprise products of the type POP-POE-POP, in particular, those commerically available under the mark PLURACOL, ofwhich each segment has a molecular weight of about 3000.

The general term polymer material covers the polymers employed alone as well as mixtures.

A first group of preferred polymers comprises polyalkylene oxides.

Among the polyalkylene oxides, polypropylene oxide (POP), formed from repeating units of the formula

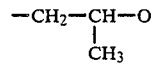

is particularly suitable.

Generally speaking, the molecular weight of the POP used is advantageously on the order of 50,000 to 100,000.

Polyethylene oxide (POE) of which the constituent units correspond to the formula $-CH_2-CH_2-O-$ is also an appropriate polymer taking into account its good properties of solvation and the high value of its dielectric constant ($\epsilon=4.5$). Its glass transition temperature varies from about $-80°$ to $-16°$ C. as a function of the molecular weight.

Given that the solubility of POE in organic solvents decreases sharply when a molecular weight of $10^6$ is exceeded, it is advantageous to use POE of a lower molecular weight, preferably on the order of 600,000.

A second group comprises polyphosphazenes, more particularly polyphosphazenes substituted with ether groups.

These are more particularly products comprising units of the type:

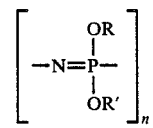

in which R and R' represent saturated hydrocarbon chains, comprising possibly one or several heteroatoms preferably O and N, possibly associated with aromatic groups, and n is the number of units in the polymer.

In the polyphosphazene group, there could also be used polyphosphazenes substituted with carrying groups of secondary amine, tertiary amine or quaternary ammonium functions, alone or in combination.

These are more particularly products comprising units of the type:

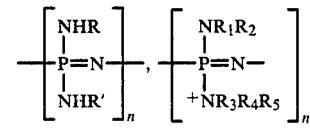

in which R, R', $R_1$, $R_2$, $R_3$, $R_4$ and $R_5$ are as defined above for R and R'.

A third group comprises polyamides based on the unit type:

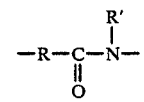

which R and R' are as defined above.

In a fourth group, the polymer used for the elaboration of the matrix is a polyalkyleneimine, more particularly a substituted polyethyleneimine comprising units of the type

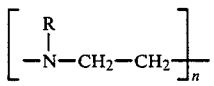

with R as defined above.

The polymers of these different types are substituted, as the case may be, it being understood that the substitutions preserve the aprotic and inert character, with respect to $O_2^-$ of the matrix.

Substituted polymers advantageously comprise perfluoroalkyl chains.

According to another embodiment of the invention, these polymers comprise charged or uncharged binding sites, permitting the transitory solvation of $O_2^-$. The binding sites playing the role of relay sites are mobile and situated at the end of the side chains, several links distance from the carbon skeleton of the base polymer. The binding site may be constituted by a unit of the polymers considered above.

Preferably, these are grafts constituted by pyridyl groups. Other grafts are of the sulphonamide type

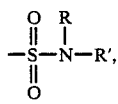

with R and R' as defined above.

Yet another group of polymers comprises a resin containing anions exchangeable with $O_2^-$.

Preferred resins are constituted by quaternary ammonium resins comprising units such as:

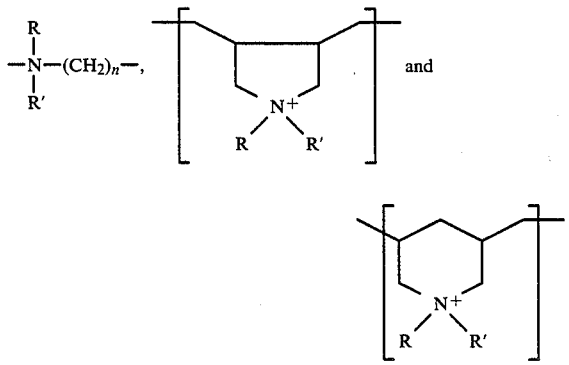

which R and R' are as defined above.

The anions of the resin may be chosen especially from among fluoride, chloride, hydroxide, iodide, tetraphenylborate, carbonate or acetate anions, previously exchanged, all or in part, with $O_2^-$ anions.

The resin employed in the polymer material could be an ionic homo- or copolymer, elaborated from a vinylic or allylic quaternary ammonium monomer, alone or copolymerized with other different allylic or vinylic quaternary ammonium monomers.

In an advantageous manner, the use of a tetraphenylborate salt and a poly(diallyldimethylammonium) salt for the preparation of superoxide compositions according to the invention permits obtaining superoxide compositions according to the invention having a high concentration of $O_2^-$ ions and both an extended existence and a good thermal stability.

According to a preferred embodiment of the invention, the polymer material comprises, in addition, at least one additive capable, particularly of augmenting its dielectric constant and/or its amorphous character or as the case may be of rendering it at least partially amorphous in the case of a crystalline or partially crystalline-based polymer, and/or still favoring the compatibility of the constituents of the composition.

Compounds suitable for this purpose comprise Polymers, more particularly of the type of those defined above, plasticizing agents or also salts, preferably of weak reticular energy.

As plasticizers, there will be mentioned polar plasticizers such as CN group-containing compounds. Studies show that a compound which bears cyano groups of the type 2,4,6-trimethoxybenzonitrile is particularly suitable.

Alternatively, the dielectric constant is augmented by using polymer materials comprising polar groups carried by the orientable side chains. Groups of this type comprise the perfluoromethyl groups.

When the polymer material comprises several polymers or copolymers, it is observed that certain superoxides allow augmenting the compatibility of the polymers. This favorable effect is observed for example with the superoxide of quaternary tetrabutylammonium.

Appropriate ionic additives, particularly for augmenting $\epsilon$ and/or the compatibility of the polymer or polymers and/or copolymers with each other and/or, as the case may be, with the superoxide salt, comprise salts of the type $A^-NR^+_4$ in which:

—$A^-$ is an anion such as $ClO_4^-$, $B(C_6H_5)^-_4$, $C_{n'}F_{2n'+1}SO^-_3$ and —R represents a saturated hydrocarbon chain, which can contain one or several heteroatoms, preferably O and N, and n' is an integer of about 1 to 10.

As neutral additives, there will be mentioned compounds comprising in particular a pyridine nucleus such as 2,2'-bipyridine.

In the case where the mechanical strength of the polymer must be increased, the polymer material defined above is present in reticulated form or also in cross-linked form comprising, particularly, a weft formed from another polymer or copolymer inert with respect to $O_2^-$ ions.

According to another preferred embodiment, the matrix containing the $O_2^-$ ions is the association of a liquid, which may be gelled, and a support constituted by a solid material permitting the percolation of the $O_2^-$ ions, that is to say the continuous migration of the $O_2^-$ ions from one region to the other of the material.

Preferred solid materials offer a good mechanical binding and comprise supports, preferably thin, for example based on glass or ceramic, such as agglomerated glass fibers, fritted glass or porous glass, or based on a wet-table polymer, porous or foamable by an impregnation solution, this polymer being inert with respect to the constituents of the solution The supported liquid may be a superoxide salt that is molten or in concentrated solution in a compatible solvent.

These supported materials offer, particularly, the advantage of a good mechanical binding, a high concentration of carriers ($O^-_2$ ions) in the support and a great mobility of these carriers. The problem of evaporation of the solvent when the solvent is of low vapor pressure or gelled, is avoided.

As indicated above, the matrix forms with the superoxide a stable material at the temperatures in question.

It will be noted that the term "superoxide" used by itself in the description and the claims designates the salt $C^+O_2^-$ formed with mineral or organic cations $C^+$.

According to a preferred embodiment of the invention, the cations $C^+$ represent mineral cations.

Appropriate mineral superoxides comprise the superoxides of the monovalent metals, more particularly of alkali metals such as $NaO_2$, $KO_2$, $RbO_2$ and $CsO_2$. Other superoxides comprise superoxides of transition metals in the form of complexes.

According to another embodiment, particularly preferred because of the good properties of compatibility of the superoxides with the polymer materials of the matrix, the cations $C^+$ represent one or several organic cations. Superoxides of organic cations particularly preferred for use in the invention comprise superoxides of quaternary ammonium used alone or in admixture.

Among the products of this type, there will be mentioned the superoxides of quaternary tetraalkylammonium $NR_4^+O_2^-$ in which R represents an alkyl radical of preferably about 1 to 10 carbon atoms.

Superoxides of this type comprise the superoxide of quaternary tetramethylammonium $TMA^+O_2^-$, the superoxide of quaternary tetrabutylammonium $TBA^+O_2^-$ and the superoxide of quaternary tetrahexylammonium $THA^+O_2^-$.

The superoxide $TMA^+O_2^-$ proves to be particularly advantageous by reason of its great stability (it melts around 97° C. and decomposes at a slightly higher temperature) and its high solubility in several organic solvents (about 0.05M in acetonitrile).

In one variant, the alkyl groups of the tetraalkylammonium cations of the superoxides used are replaced by ether groups, for example of the structure $-[(CH_2)_2-O]_n-CH_3$ in which n is an integer, preferably of about 1 to 5.

According to another variation, the superoxides used for the seeding are dissolved by the solvent or solvents used for their preparation, usually pyridine.

This solvation leads advantageously to a favorable effect on the stability of the system.

Compositions of the invention are prepared by incorporatiog $O_2^-$ anions in a matrix as defined above. This operation of incorporation corresponds to a seeding of the matrix with $O_2^-$ ions.

According to a modified embodiment, the incorporation is effected by chemical means in the presence of a solvent in which the matrix and the superoxide are soluble or may be rendered soluble with the aid of additives.

The solvent employed is an aprotic solvent such as pyridine, benzene or toluene

Whnn the superoxide salt is a mineral salt, to facilitate the rendering soluble of the salt and/or to augment the size of the cations so as to diminish the potential wells that they constitute for the anions, there is used according to the conventional methods a complexing agent for the alkali cations such as a crown-ether or a cryptan.

According to another embodiment, the seeding of $O_2^-$ is effected by electrochemical means by cathodic reduction of molecular oxygen according to the method described in U.S. Pat. No. 3,102,140 in the name of Callery Chemical Co.

In a preferred manner, the electrochemical incorporation of $O_2^-$ anions in the matrix is realized by replacing pre-existing electroactive anions in the matrix, the said anions being eliminated by anodic oxidation in proportion to the creation of $O_2^-$ ions at a cathode submitted to a flux of gaseous or dissolved oxygen.

To prepare the derivatives of superoxides in the form of a membrane, one proceeds to the evaporation of the solvent or solvents of a mixture constituted on the one hand by a solution of the material constituting the matrix and on the other hand by a solution of superoxide salt, these solutions being degasified.

The evaporation is conducted, preferably, under a current of dry gas such as nitrogen and at a controlled temperature. There is used a planar support of a material inert to the reagents employed, for example polytetrafluoroethylene (PTFE). After evaporation of the solvent or solvents, the membranes formed are dried.

According to a preferred embodiment of the invention, which permits augmenting the conductivity, the membrane is subjected to at least one annealing operation, preferably at a temperature slightly lower than the temperature of fusion of the material of the seeded matrix, if the superoxide is not degraded at this temperature.

To improve the mechanical binding of the polymer material, a weft to support the base polymer is effected with the aid of another polymer or copolymer according to the conventional techniques.

The material may also be reticulated before, or, as the case may be, after incorporation of the superoxide, particularly by irradiation or by UV photoreticulation.

The superoxide of quaternary tetraalkylammonium $NR_4^+O_2^-$ may be prepared in a conventional manner by electrolysis of a tetraalkylammonium halide $NR_4^+X^-$ in which R is as defined above and $X^-$ represents a halide ion and reduction of the oxygen or, according to another variant, by a solid-solid reaction followed by an extraction, as described in Inorg. Chem. 1964, 3, 12, 1798-1799, and 1983, 22, 18, 2577-2583.

The superoxides $NR_4^+O_2^-$ may be prepared by a metathesis reaction between:

a—a quaternary ammonium salt, of which the anion inert to $O_2^-$ is preferably chosen from the anions $F^-$, $I^-$, $OH^-$, $NO_3^-$, $ClO_4^-$, $BPh_4^-$, $CH_3COO^-$, $CO_3^{--}$ and b—an excess of superoxide the cation of which is an alkali metal cation, preferably $K^+$ or a quaternary ammonium cation, preferably $TMA^+$.

This metathesis may, in fact, be effected as a solid-solid reaction, according to the above U.S. patent, followed by recovery of $NR_4^+O_2^-$ in liquid $NH_3$.

According to a novel provision of the invention, the metathesis reaction is conducted in an organic solvent such as benzene, toluene, or as the case may be, dimethylsulfoxide DMSO, and preferably, in pyridine.

The electrochemical study of the above compositions based on superoxide has permitted determining their properties of high anionic conductivity and this, in an advantageous manner, in a temperature range from ambient to about 100° C.

These compositions permit more particularly the diffusion of oxygen in the $O_2^-$ form while constituting an impermeable barrier to the other gases not ionizable under the same conditions as $O_2$.

The invention therefore seeks to provide new electrolytic materials based on compositions of superoxides such as defined above.

It is to be noted that the constituents of the electrolytic material offer a good chemical stability with respect to $O_2^-$ but equally with respect to the chemical species that may be produced by the reactions of $O_2^-$ with the impurities of the material, in particular with respect to the peroxide species (peroxides, hydroperoxides, peroxydates) resulting from the disproportionation of the superoxides. The presence of any compound favoring or catalyzing the disproportionation of the superoxides must therefore be avoided.

The electrolytic material may be, furthermore, a cationic conductor if the cations are not too bulky and if their diffusion does not limit the anionic conductivity.

According to another embodiment of the invention, this electrolytic material is rendered an electronic conductor for example by incorporation of electronically conducting particles such as particles of carbon or of magnetite $Fe_3O_4$. These materials offer the advantage of being able to be used in the apparatus employing a difference of partial pressure of oxygen instead of a difference of electric potential.

This electronic conductivity is not, however, desirable when there is used an electric generator in the circuit, or when it is sought to generate an electric voltage, as it would lead to a loss of energy or to an auto-discharge.

In benefiting from the filmogenic properties of the matrix materials, the electrolytes of the invention are advantageously prepared in the form of membranes, thus permitting the provision of vast surfaces.

Preferred membranes have thicknesses less than 500μ, in particular on the order of 10 to 500μ, advantageously about 30 to 100μ.

Matrix materials particularly advantageous for the transportation of transparent homogeneous membranes comprise a polymer material, in particular, a polyalkylene oxide such as defined above.

Electrolytic membranes of high conductivity comprise a copolymer, more particularly a statistical copolymer with OE (ethylene oxide) and OP (propylene oxide) units.

The percentage of OP units is advantageously at least about 5%, preferably, about 40% in the copolymer whose molecular weight is more particularly on the order of 5,000 to 500,000.

Other membranes comprise a mixture of polymers and one or several additives.

Preferred weight proportions of the consitutents of the membrane, mixture of polymers/additives/superoxides, are about 6/1/2.

Advantageous membranes of this type are based on POE and comprise another polymer such as POP, preferably according to a ratio of about 4/2.

As a composition, there will be mentioned POE/POP/additive such as THAP (tetrahexylammonium perchlorate)/superoxide salt such as $TBAO_2$ in the weight proportions of about 3 to 5/2/1/2 or also, POE/POP/additive such as THAP/superoxide such as $KO_2$/complexing agent such as the crown ether 18-crown-6 in the proportion of about 3 to 5/2/1/0.4/0.4.

The invention also seeks apparatus or electrochemical cells for selective transport of oxygen using, as transporters of oxygen and of current, $O_2^-$ ions moving in an electrolytic material as defined above.

Preferred cells are characterized in that they comprise the electrolytic material, advantageously in the form of a membrane, compressed between two coextensive electrodes face to face with the said film, these electrodes being constituted by a conductor material permeable to gas, porous, inert with respect to the electrolytic material at a temperature less than 100° C. and unoxidizable, at least as concerns the anode.

The materials of the two electrodes are the same or different.

The electrolytic chain elaborated starting from the electrolytes of the invention corresponds to the following sequence: (medium 1) cathode/electrolyte/anode (medium 2).

The molecular oxygen of medium 1 is reduced at the cathode to the state of $O_2^-$ anion by a monoelectronic reaction $O_2 + e^- \rightarrow O_2^-$ that is quasi-reversible in the absence of protons in the medium.

The $O_2^-$ ion diffuses in the electrolyte and becomes discharged at the anode according to a similarly monoelectronic reaction, quasi-reversible, corresponding to the equation: $O_2^- \rightarrow e^- + O_2$. The oxygen may combine with the metal or material of the anode if this latter is oxidizable, or be evolved in gaseous form in the contrary case.

It will be noted with interest that the overall reaction corresponds to the transfer of one oxygen molecule for each electron supplied in the circuit whereas four electrons were necessary in the previous technique.

In addition, it will be noted that there is at no time produced a rupture of the oxygen-oxygen bond, the superoxide ion being a molecular ion.

The use of reversible processes, both at the cathode as well as at the anode, permits reducing the activation energy to be supplied to the system either in an electrical form or in a thermal form (saving in energy cost of operation), or by catalytic means (saving in investment).

Generally speaking, it is thus possible significantly to diminish the overvoltages at the electrodes, to lower the operating temperatures and to simplify, in the electrochemical apparatus employed, the technology of the electrodes that will not have to be assured a particularly delicate electrocatalyst in the case of $OH^-$ ions.

The electrode materials are especially chosen from the materials capable of accelerating the redox reaction $O_2$ (adsorbed) $+ e^- \rightarrow O_2^-$ and not involving the dissociative chemisorption of the oxygen molecule.

Appropriate materials comprise gas-permeable materials based on carbon, for example vitreous carbon or graphite, that may be mechanically supported by a conducting or non-conducting network, for example a fabric of polypropylene.

The carbon may be incorporated in the form of particles and/or fibers dispersed in a polymer material.

The conductor material based on carbon may also be in the form of a layer that may be woven, a felt or a paper of carbon.

Other appropriate materials comprise a not very oxidizable metal in a dispersed form in a polymer material or in the form of a layer which may be woven.

For the cathode, the metal may be formed from steel covered with a deposit of, for example, platinum or nickel.

According to a modified embodiment, the electrodes are formed from a combination of materials.

One type of combination comprises a weft of a polymer, having high resistance properties, supporting a very thin film of electronically conducting polymer, itself loaded with a powder of vitreous carbon or with another product assuring a good electronic transfer.

According to another type of combination, the electrodes are formed from one or several materials conferring on them properties of conduction at once electronic and ionic with respect to $O_2^-$.

According to another variant, the electrochemical apparatus comprises interposed between the electrode and the electrolyte a film of composite conductor, electronic and ionic, in which $O_2$ is soluble, thus permitting effecting the reduction of $O_2$ in a great volume and not only at the electrode-electolyte surface.

According to yet another variant, the electrodes are formed as an asymmetric system, the cathodic side favoring the flow of gas so as to limit the polarization of the gaseous phase and to restrict the electrode reactions to the reduction of $O_2$ by a single electron, and the anodic side favoring the oxidation of $O_2^-$ and the departure of gaseous oxygen.

Satisfactory performance on an industrial scale is obtained with the aid of apparatus having vast membrane surfaces and high compactness.

According to an advantageous process for utilization, these apparatus are present in the form of small modules of several tens to several hundreds of $m^2$ each.

These are particularly cylindrical modules where the membrane is spirally wound, of the type of those used in conventional gaseous permeation. In these cylinders, the wound strata succeed one another advantageously as follows: cathode/membrane/anode/membrane/-cathode . . . The cathodes on the one hand, the anodes on the other hand are permeable to the gases and each extend from one side of the cylinder in the axial direction so as to be connected to the current conductors. The circulation of the gases is effected according to the method known as crossed currents interiorly of the porous electrodes, the oxygen being collected on the axis of the cylinder.

Another type of suitable module comprises the forming of the membranes in the containers in the form of cathode/membrane/anode sandwiches, folded accordion-style in the container constituted for example by the faces of gas-tight insulating material and by conducting faces distributing current and gas.

The modules are grouped in series, in parallel or in parallel series.

According to yet another aspect, the invention contemplates a process for the selective transfer of oxygen from a first medium to a second medium according to which there is used the electrochemical reduction of oxygen leading to the transitory formation of $O_2^-$ ions, the diffusion in the form of $O_2^-$ in an electrolytic material such as defined above, which constitutes moreover a barrier practically completely impermeable to other gases, and the oxidation to oxygen of the $O_2^-$ ions.

In a preferred embodiment of this process, there is imposed a potential difference, with the aid of an external electric generator, to the terminals of the electrodes of a cell such as that defined above, separating the media described earlier.

The electrode E1 used as cathode is adjacent the first medium and that used as anode E2 is adjacent the second medium.

Under these conditions, the oxygen of medium 1 is consumed at the level of the electrode E1: an electrochemical reduction reaction transforms it into $O_2^-$ ions that migrate to the electrode E2 where an electrochemical reaction opposite to the preceding one is produced (oxidation of the anion to oxygen that is evolved in the medium 2).

The net result of this chain of processes is a transfer of oxygen from the medium 1 to the medium 2 obtained at the price of a consumption of electrical energy.

It will be noted that it is also possible by these processes to compress the oxygen in the anodic compartment.

According to another embodiment, there is assured the selective transfer of oxygen from a first gaseous medium at a partial pressure of oxygen itself elevated to a second medium at lower partial pressure of oxygen, by maintaining a difference of partial pressure between the considered media separated by an electrochemical cell, such as defined above. This difference in partial pressure supplies an electric voltage E to the terminals of the electrodes.

This voltage may be used as an electric generator: a concentration cell functionin between two imposed partial pressures $P_1$ and $P_2$, or a fuel cell in the case where oxygen produced at the electrode E2 is consumed by an irreversible chemical reaction.

The voltage that appears between cathode and anode when there exits a difference in partial pressure of oxygen between the two gaseous media may be used to make a gauge for oxygen functioning at ambient temperature. In this case, the partial pressure of oxygen of one of these media serves as a reference. The Nernst equation gives the value of the measured voltage (without current flow)

$$E = \frac{RT}{F} \log_e \frac{P_1}{P_2}$$

the number of electrodes implicated in the electrochemical chain here being 1, R being the ideal gas constant, F the faraday value and T the absolute temperature. It should be noted that the voltage E delivered by this type of gauge is four times higher than that furnished by the gauges using an electrolyte conductive with $OH^-$ ions or $O_2^-$ ions.

In a particular embodiment, when there exists a difference of oxygen partial pressure between two gaseous media separated by the electrochemical cell described above, the two electrodes are connected by a passive external circuit comprising a conductor of weak electrical resistance and a switch. Such an apparatus permits controlling (namely regulating or interrupting) the flow of oxygen that passes from the medium 1 comprising the greater partial pressure of oxygen toward the medium 2. When the switch is in closed position, the cell is short-circuited and the oxygen is transferred from the medium 1 to the medium 2 migrating in the form of superoxide, the electrons released at the electrodes flow in the exterior conductor. When the switch is in open position, a voltage occurs at the electrodes, but the electrons are unable to flow in the external circuit, the flow of oxygen between the medium 1 and 2 is interrupted (it is in fact limited to the permeation flow of the neutral molecular oxygen across the electrolyte membrane).

The "all or nothing" control thus realized may be refined by the introduction of a variable resistance in series in the external circuit: the measure of the current permits controlling in a very precise manner the oxygen flow that is transferred from the medium 1 to the medium 2.

It is clear that this very simple scheme may lead to an actual controlled system permitting for example the stabilizing or programming of the partial pressure of oxygen of one of the two media.

According to yet another variant, if the electrolytic medium permits not only the diffusion of oxygen in the anionic form but also the transport of electrons, the system may then function as a "semi-permeable" membrane selective for oxygen. The term semi-permeable is not taken here in the conventional sense for permeation: the selectively of the membrane for oxygen is not due to a preferential diffusion of the dissolved neutral molecular oxygen but to the presence of the mobility of the oxygen anions and of the electrons.

The general principle of operation is the following: the electronic conductivity leads to a partial short-circuit of the membrane. This short-circuit gives rise, under the action of a difference of oxygen partial pressure between the two faces of the membrane, to electronic and ionic currents that cancel each other out but the net balance of which is a transfer of oxygen from one side to the other of the membrane. The semi-permeability flow increases with temperature. The electronic conduction in the same material has the advantage, compared to the case where the electrons return through an external circuit, of uniformly distributing the current in the membrane.

More precisely, if there exists a difference in partial pressure of oxygen between the two faces of the membrane, the oxygen may be reduced to an oxygen anion in contact with the membrane on the high pressure side, then migrate across the membrane by diffusion before being oxidized to oxygen on the low pressure side. The liberated electrons on the low pressure side may then migrate toward the high pressure side by diffusion across the electrolytic medium of mixed conductivity (ionic and electronic).

The selectivity of the oxygen transfer provided by the apparatus of the invention renders it particularly appropriate for applications concerning the separation of oxygen.

Such applications comprise the production of oxygen by concentration from air, particularly dry air, preferably low in content of acidic gases such as $CO_2$, $SO_2$ or $SH_2$, for industry or in the medical field, the purification of gas containing oxygen, the introduction of controlled quantities of oxygen into a gas, the analysis of gaseous media.

Other characteristics and advantages of the invention are related in the examples that follow and in referring to the figures.

FIG. 1$b$ shows the magnification of a part of the cell of an apparatus according to the invention shown in FIG. 1$a$.

FIG. 2$b$ shows a fold of the modular element of FIG. 2$a$ of the sandwich type.

FIG. 3 shows the same module in section.

EXAMPLE 1

Preparation of a superoxide composition based on POE-POP/$TBAO_2$ in the form of a membrane There are prepared a polymer solution 1 and a tetra-n-butylammonium superoxide solution 2, by proceeding as follows:

Solution 1

There is dissolved 4 g of POE of molecular weight 600,000 (Aldrich), 2 g of POP (Hercules Co., under the name of Parel 58) and 1 g of tetra-n-heyylammonium perchlorate (Alfa Ventron) in a sufficient amount of pyridine (Prolabo) to make 100 ml of solution. This solution is strongly agitated for about 15 hours.

Solution 2

There is mixed 1g of tetra-n-butylammonium fluoride (TBAF) trihydrate (Fluka) with 2.5 g of potassium superoxide (96.5% pure) (Alfa Ventron) in a sufficient quantity of pyridine (Prolabo) to make 15 ml of solution. The metathesis reaction is allowed to take place with agitation for 10 to 30 mins. It is centrifuged, and the liquid portion is recovered. Next, the solid is dissolved in 15 ml of pyridine. After centrifuging, the liquid portion is recovered. The solution obtained by recombining the two liquid fractions, being 30 ml in all, contains about 0.6 g of tetra-n-butylammonium superoxide.

Solution 2 is mixed with 30 ml of solution 1 by agitating for 10 to 30 mins. A vacuum is created above the solution (about 20 mm Hg) to evaporate about 50% of the solvent. Heat may be applied to a maximum of 35° C. to accelerate the evaporation. About 30 ml of yellow, viscous solution is obtained that is poured into a flat-bottom vessel of polytetrafluoroethylene. The solution is evaporated in a stream of dry nitrogen for a period of 12 to 15 hours.

The membrane is turned over and the evaporation is continued for at least 3 hours.

A film in the form of a very pale yellow homogeneous membrane that contains POE/POP/THAP/$TBAO_2$ is thus obtained having the following weight ratio: 4/2/1/2. The conductivity of this membrane at 20° C. is $4 \times 10^{-7} \Omega^{-1} cm^{-1}$ and at 50° C. is $5 \times 10^{-6} \Omega^{-1} cm^{-1}$.

This membrane lends itself well to being rolled between two rollers of polytetrafluoroethylene to thicknesses on the order of 20 microns.

EXAMPLE 2

Variant of the preparation of solution 2 (TBAS)

Use of the fluoride anion as the departure anion

Solvent: toluene.

4 m of TBAF trihydrate is added to 300 ml of toluene and about three-fourths of the toluene is distilled off azeotropically at atmospheric pressure. The solution is cooled and $KO_2$ is added. The mixture is agitated for about 8 h, then filtered under nitrogen so as to recover the solid products. An identical volume of dry cyclohexane is added to the filtrate. Cloudiness develops. It is cooled to $-20°$ C. to crystallize the product which is formed. The requisite quantity of $TBAO_2$ is redissolved in pyridine to obtain solution 2.

The tetrabutylammonium superoxide (TBAS) compositions could also be prepared by using other less hydrated departure anions than fluoride, for example carbonate, iodide or acetate, according to the following operating procedure:

Use of carbonate as departure anion

Tetrabutylammonium carbonate (TBAC) is first prepared by bubbling gaseous $CO_2$ in a methanolic tetrabutylammonium hydroxide solution, then by evaporating the methanol. The white, crystallized TBAC is then dried, and the TBAC is redissolved in pyridine (a portion of the product remains in suspension) and there is added to this solution an excess of powdered potassium superoxide. After agitating the solution for several minutes, the solution is filtered to separate $KO_2$ and $K_2CO_3$ and a solution of TBAS is present in the pyridine.

The reaction is written:

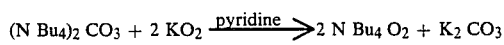
$$(NBu_4)_2 CO_3 + 2 KO_2 \xrightarrow{\text{pyridine}} 2 NBu_4 O_2 + K_2CO_3$$

Use of iodide as departure anion

The $O_2^-$ and $I^-$ anions may also be exchanged in certain very particular cases where the lattice energy of the products formed figures prominently.

If powdered potassium or sodium iodide is added to a solution of TMAS in pyridine, or better yet in aceonitrile, the immediate precipitation of tetramethylammonium iodide (TMAI) is observed, the lattice energy of TMAI being very great. On the contrary, in dimethylsulfoxide, TMAI is much more soluble and the separation of TMAI from the superoxide formed is much more difficult. This rapid precipitation of TMAI in $CH_3CN$ provides another novel means for preparing TBAS and other quaternary ammonium superoxides. It suffices in fact to exchange $O_2^-$ and $I^-$ between TMAS and tetrabutylammonium iodide TBAI in $CH_3CN$. The TMAI precipitates, and, after filtration, there results a solution of TBAS in $CH_3CN$. The reaction is as follows:

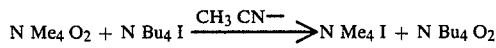
$$NMe_4 O_2 + NBu_4 I \xrightarrow{CH_3 CN} NMe_4 I + NBu_4 O_2$$

These reactions with iodides may not be applied in the presence of hydriodate. The ammonia must be quaternary (4 groups other than H on the nitrogen atom).

Use of acetate as departure anion

Quaternary superoxide solutions may also be prepared from corresponding acetates. For example, in the case of $NBu_4O_2$, the preparation method is as follows: Tetrabutylammonium acetate is first made by adding glacial acetic acid dropwise in a methanolic tetrabutylammonoium hydroxide solution until the pH is about 4. The methanol is driven out in a rotary evaporator without exceeding 50° C., then a little acetonitrile is added to the precipitate, which is driven out again.

The acetate is then placed in the pyridine and powdered $KO_2$ is added. The acetate is insoluble in the pyridine, like the $KO_2$, but the exchange between the $O_2^-$ and $CH_3COO$ anions takes place rather rapidly as the solution is yellow colored and contains tetrabutylammonium superoxide.

The reaction, which is written:

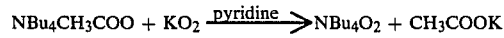
$$NBu_4CH_3COO + KO_2 \xrightarrow{\text{pyridine}} NBu_4O_2 + CH_3COOK$$

is nevertheless not quantitative.

The methods described above are relatively mild since the reactions are produced at ambient temperature and thus do not result in rapid degradation of the superoxides in solution during their preparation. Nevertheless, the ammonium superoxides could be extracted from the solution in which they were prepared, so as to isolate them from the various constituents (anions, solvents . . . ) of the reaction medium, which would cause a slow degradation of the superoxide.

EXAMPLE 3

Preparation of a superoxide composition based on poly(diallyldimethylammonium) chloride The reagents used are:

Poly(diallyldimethylammonium) chloride (abbreviation PDADMAC) in a 15% aqueous solution (Polysciences Ref. 6515, Warrington, Pa., U.S.).

Sodium tetraphenylborate (Ref. 72020 Fluka-CH)

Solution of tetrabutylammonoium superoxide in pyridine prepared by metathesis between tetrabutylammonium fluoride pentahydrate and potassium superoxide.

Pyridine (Prolabo-France)

Poly(diallyldimethylammonium) tetraphenylborate (abbreviation PDADMA-TPB) is first prepared by exchange of $Cl^-$ and $BPh_4^-$ ions in water according to the reaction:

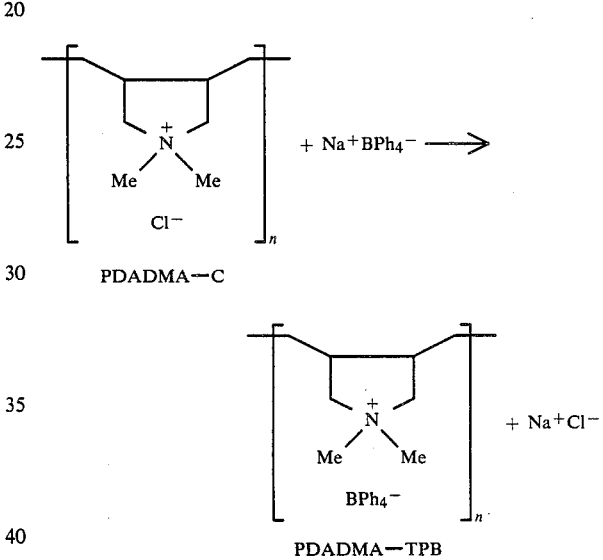

The PDADMA-TPB precipitates quantitatively in the form of white powder. It is dried by heating under vacuum at 60° C. for 24 h. The replacement of the $Cl^-$ ions by the $BPh_4^-$ ions is effected at almost 100%.

The dry PDADMA-TPB is dissolved in pyridine (or DMSO) at 20° C., then a solution of tetrabutylammonium superoxide $N(C_4H_9)_4O_2$ is added to the solution. The poly(diallyldimethylammonium) superoxide (abbreviation PDADMA-S) precipitates in the form of a whitish powder. It is dried under vacuum at 20° C.

The total percentage of $Cl^-$ or $BPh_4^-$ anions replaced by $O_2^-$ is measured by volumetrically proportioning the $O_2^-$ ions. The volume of oxygen evolved is measured when the solid and dry product obtained is made to react with an aqueous ferric chloride solution $FeCl_3$ (1M) and hydrochloric acid (1M).

The overall reaction is as follows:

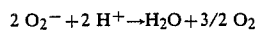
$$2 O_2^- + 2 H^+ \rightarrow H_2O + 3/2 O_2$$

The measurements effected show that in the PDADMA-S obtained by two successive metathesis reactions, about 60% of the anions present in the polymer are $O_2^-$ anions, the remaining anions being $BPh_4^-$ (since the first exchange of ions is almost total). This corresponds to about 2.5 milliequivalents of $O_2^-$ per gram of polymer although the molar mass of the $BPh_4^-$ anions is quite high.

The PDADMA-S, maintained under vacuum at 20° C., remains intact for several weeks and its physical appearance is not changed up to 170° C. (Kofler bench test). This thermal stability is clearly superior to that of the tetrabutylammonium superoxide (TMAS) which melts at 97° C. and is decomposed toward 100° C. The quaternary polyammonium thus prepared, about 60% of the anions of which are $O_2^-$ ions (the other anions are $Cl^-$ and $BPh_4^-$) has excellent thermal stability and a very extended existence.

So as to render the $O_2^-$ ions mobile in the polymer, PDADMA-S is plasticized by low weight polymers (between about 400 and 1,200) which solvate the $O_2^-$ ions so as to separate these latter from their counter-ions belonging to the skeleton. These plasticizers may be chosen, for example, from polymers capable of solvating the $O_2^-$ ions by hydrogen bonding, for example polyethyleneimine prepared by alkaline hydrolysis of polyoxazoline according to the method described by T. SAEGUSA et al., J. Am. Chem. Soc. (1985), 107, pp. 3823–3828.

The PDADMA-S may also be rendered amorphous by other means such as:

Replacing the methyl groups by groups having several —$CH_2$— linkages, for example butyl or hexyl.

Copolymerizing diallyldimethylammonium chloride with a vinyl ether or another vinylic monomer compatible with the $O_2^-$ ions (example: methyl-vinyl-ether perfluorate).

EXAMPLE 4

Film based on POPO/TBAO$_2$

One proceeds as in Example 1, by subjecting a solution of POP (3 parts by weight) and a solution of TBAO$_2$ (1 part by weight) to a coevaporation operation.

The membrane obtained is in the form of a sticky paste of which the mechanical strength is increased with the aid of an unwoven mat of polypropylene fibers introduced before evaporation.

EXAMPLE 5

Transfer of oxygen across a membrane seeded with $O_2^-$ anions, by application of an electric voltage to the terminals of an electrochemical cell provided with this membrane Tests have been carried out with the assembly shown in FIG. 1a. FIG. 1b shows an enlargement in section of a part of the electrochemical cell.

The membrane (1), the preparation and composition of which are described in Example 1, has a diameter of 60 mm and a thickness of about 150 microns. It is pressed between two non-woven layers of carbon fibers (2a) and (3a) (International Paper) that play the role of porous electrodes. The sandwich of carbon fibers-membrane-carbon fibers is itself pressed between the discs of fritted stainless steel (17) and (18).

The chamber (19) that comprises the inlet and outlet conduits for gas (20) and (21) has a volume of about 50 cm$^3$ and plays the role of the cathodic compartment.

The chamber (22) is connected by the gas outlet conduit (23) to a pressure recorder and its total volume, that is to say including the tubes, connections and the dead volume of the recorder is 3 cm$^3$. It plays the role of anodic compartment.

The assembly of the cell is thermoreglated to 48.0°±0.1° C. by circulation of water in the brass blocks (24) and (25).

Before placing the device onstream, the chamber (19) is filled with oxygen at 1 bar and the chamber (24) is filled with oxygen at 1005 mbar. The two compartments are rigorously sealed.

After stabilization of the temperature and the pressure, an electric potential difference of −0.8 V is applied between cathode and anode. The current intensity is 300 µA at the outset of the experiment and is rapidly stabilized around 60 µA.

After passage of a quantity of electricity of $1.67 \times 10^{-1}$ C measured for 30 mins by a coulomb meter, it is ascertained that the pressure in the chamber (22) has changed from 1,005 to 1,017 mbar, this corresponding to the production of $1.37 \times 10^{-6}$ mole of oxygen for $1.73 \times 10^{-6}$ Faraday having traversed the cell. The faradic ratio, about 1, indicates that the transfer of oxygen has thus been effected by means of superoxide anions $O_2^-$.

EXAMPLE 6

Accordion-type module utilized as an electrochemical apparatus for separating oxygen from the air FIGS. 2a and 2b concern a variation of an accordion-type modular apparatus and show respectively, a broken-away view of a module and the detail of a fold in section.

The module is composed of an electrolytic membrane-electrode assembly (1,2,3) folded accordion style inside a parallelepipedal, sealed container comprising four insulating surfaces (4,5,6,7) and two conducting surfaces (8,9) serving as inlets of both current and gas. The membrane (1) of the type described in Example 1 is pressed in a sandwich between two layers of porous electrode material (2) and (3), for example graphite cloth. The composite film thus formed is folded accordion style. It is useful to interpose, between the folds, layers (14) of an electric conducting material very readily permeable by gases, for example, a corrugated metallic grid, the role of which is, on the one hand, to maintain between the folds of the film a space permitting an easy circulation of the gases and to optimize its passages therethrough, and on the other hand, to furnish electric contacts that are well distributed over the surface of the electrodes.

The two extremities of the stack thus provided perpendicular to the folds (10 and 11) are rendered gas-tight, for example, by immersing them in an electrically-insulating resin of the epoxy or silicone type. They are applied in a sealing manner against the two surfaces (4) and (5) of the container.

Moreover, each of the extremities of the composite electrode membrane parallel to the folds (1 and 13) is joined in a sealed fashion and over all its length to one of the insulating plates (6 and 7) of the container.

Figure 1A:
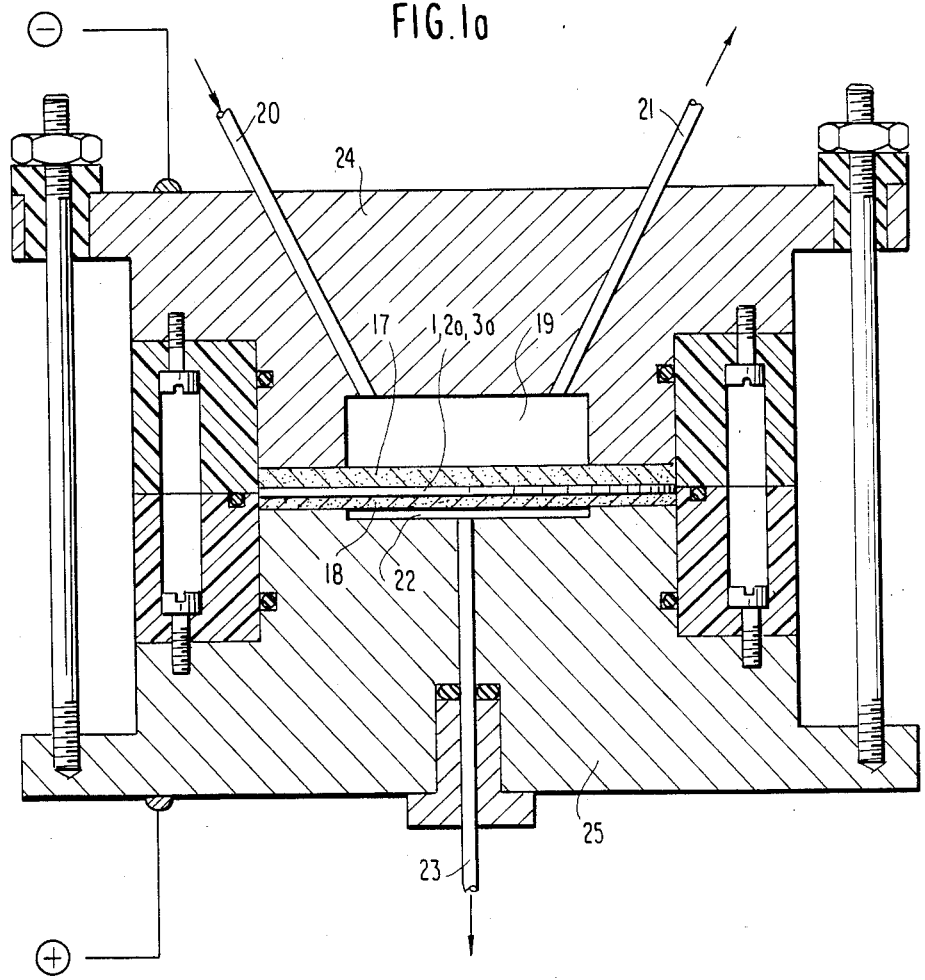
Figure 1B:
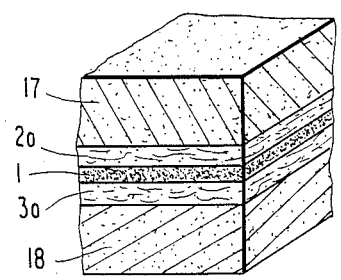
Figure 2A:
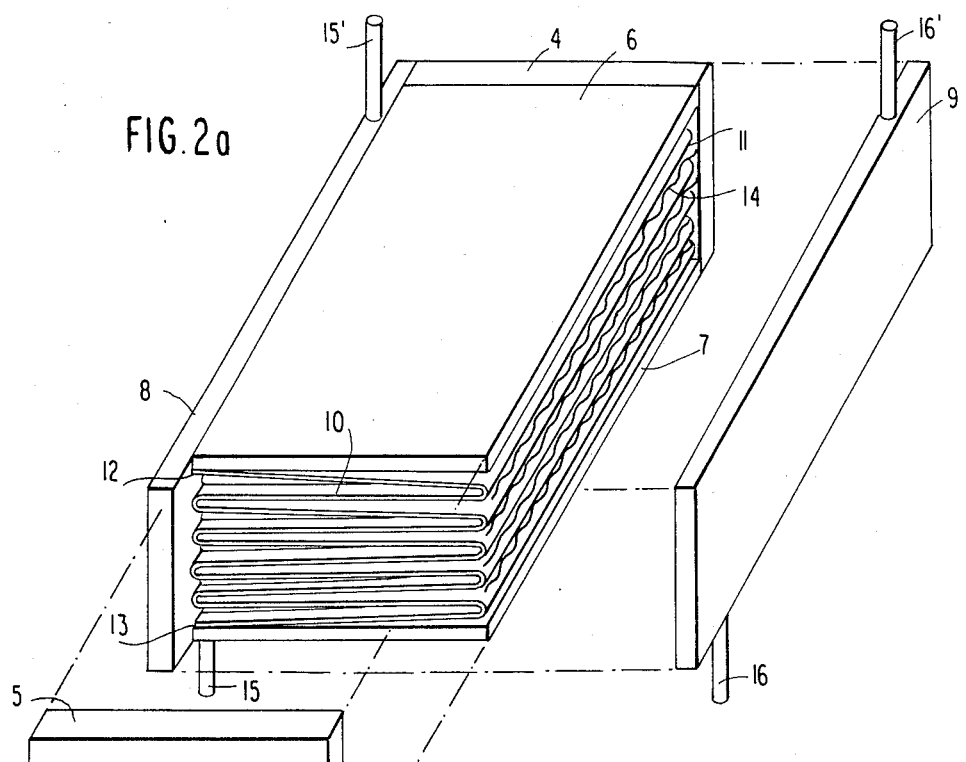
FIG. 2b shows how each of the electrode layers (2) and (3) surrounding the electrolytic film (1) is in electric contact at the level of the folds with one of the two conducting surfaces (8) and (9).
Figure 2B:
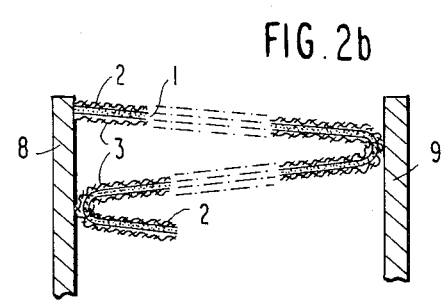
Figure 3:
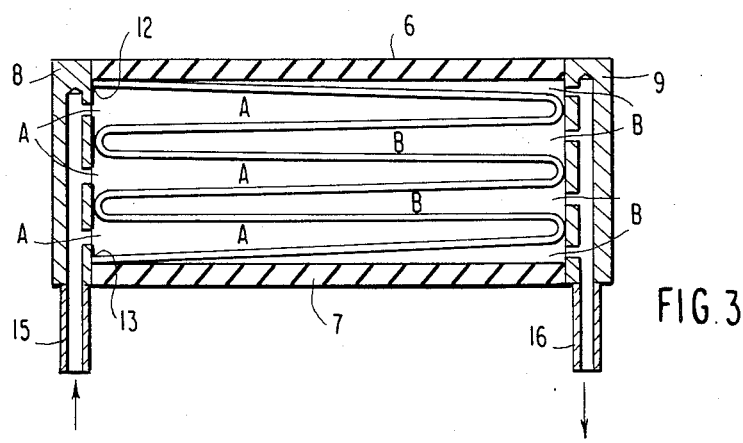
FIG. 3 shows a section of the module in the plane perpendicular to the fold situated at the level of the gas conduits (15) and (16).

It also shows how the container/film accordionstyle composite system delimits two regions A and B insulated the one from the other with respect to gases and electrically.

Channels are arranged in the surfaces (8) and (9), so as to cause to communicate each of the compartments A and B with the nipples (15), (15') and (16), (16') respectively, which nipples are connectible to external gas circuits.

The modul thus constructed is used to produce oxygen from the air. The mode of operation is the following: air slightly compressed to overcome the losses of charge (1.5 bar absolute) flows into the compartment A, entering via nipple (15), exiting via nipple (15'). The plates (8) and (9) are respectively connected to the — and + symbol terminals of a direct current generator which can deliver a voltage of about 1 V between these plates. The plate (8) distributes the current over the electrode (2) the length of the folds which are adjacent to it and thanks to the interleaved conductive layers (14) internal to the compartment A.

In the same way the plate (9) distributes the current over the electrode (3) the length of the folds which are adjacent to it and thanks to the interleaved conductive layers (4) internal to the compartment B.

The oxygen from the air circulating in the compartment A is reduced to superoxide anions at the level of the layer of electrodes (2) (cathode). The nitrogen, which does not undergo any electrochemical reaction is purged in a continuous manner through the outlet 15' where there is obtained an air deficient in oxygen.

The superoxide anions which have migrated across the membrane (1) are oxidized at the level of the anode (3) to produce oxygen which is evolved in gaseous form in the compartment B and may be collected at one of the outlets (16) and (16').

Such modules may be easily assembled in series or in parallel according to the characteristics of the current generator that is used.

EXAMPLE 7

Application of the apparatus of Example 3 as an oxygen gauge

An apparatus of the type according to Example 3 is used containing as electrolyte POE/POP/THAP/TBAO$_2$ at the ratio of 4/2/1/3 parts by weight.

Membrane discs are used at 20° C., of 3 cm$^2$ surface and of about 150 microns thickness. The membrane thus provided is lightly pressed between two discs of conducting carbon cloth of the type commercially available from the Société le Carbone Lorraine under the reference TCS 80 (or also TCM 128) or that distributed by the International Paper Co. The carbon discs are themselves held in place by two thin gratings of stainless steel covered with gold by cathodic spuddering, that are connected to the measuring circuit (numerical voltmeter).

This apparatus is sensitive to any difference of chemical potential (partial pressure of oxygen in the present case) between the upstream and downstream media separated by the membrane, and supplies a potential difference to the terminals of the electrodes. There has been noted the appearance of a difference of potential of 39±1 mV when the upstream medium is constituted by pure oxygen value of 39.3 mV calculated according to the Nernst equation for a monoelectronic transfer. It follows therefrom that there is observed a reduction of oxygen to $O_2^-$ on the high pressure side and an oxidation of $O_2^-$ to $O_2$ on the low pressure side of the membrane. There is obtained 90% of the response in less than 20 seconds when passing from air to pure oxygen.

The experiment is readily performed by maintaining one of the sides of the membrane under circulation of pure oxygen, while the other side is alternatively subjected to a circulation of pure oxygen and of another gas of which one wishes to measure the oxygen content.

We claim:

1. A solid electrolytic material for selective transfer of $O_2^-$ ions, comprising a matrix chemically stable to $O_2^-$ ions and mobile $)_2^-$ ions incorporated in said matrix, said matrix comprising a solid macromolecular electrolytic substance, or a liquid or gelled electrolyte containing superoxide salt and carried on a porous support, said material conducting $O_2^-$ ions at operating temperatures up to about 100° C.

2. A solid electrolytic material according to claim 1, containing $O_2^-$ anions at a concentration of about $10^{-2}$ to 2 milliequivalents per gram, absent applied electrical potential.

3. A solid electrolytic material according to claim 1, in the form of a membrane having a thickness of 10 to 500 μm.

4. A solid electrolytic material according to claim 1, further comprising at least one inorganic cation associated with said $O_2^-$ ions in said matrix.

5. A solid electrolytic material according to claim 4, wherein said inorganic cation is a metal cation selected from $Na^+$, $K^+$, $Rb^+$, $Cs^+$, or a transition metal complex cation.

6. A solid electrolytic material according to claim 1, further comprising at least one organic cation associated with said $O_2^-$ ions in said matrix.

7. A solid electrolytic material according to claim 6, wherein said organic cation is a quaternary ammonium cation $NR_1R_2R_3R_4^+$, where $R_1$ to $R_4$ represent identical or different radicals, excluding H radicals.

8. A solid electrolytic material according to claim 7, wherein $R_1$ to $R_4$ are identical saturated alkyl radicals $C_nH_{2n+1}$, n being an integer from 1 to 6.

9. A solid electrolytic material according to claim 7, wherein at least one of $R_1$ to $R_4$ contains ether groups with the formula $-(CH_2-CH_2-O)_n-CH_3$, where n is an integer of 1 to 5.

10. A solid electrolytic material according to claim 1, wherein said solid macromolecular electrolytic substance is based on a polymer material that is at least partially amorphous at said operating temperatures, possessing a high dielectric constant and forming, after incorporating said $O_2^-$ ions, a phase with a glass transition temperature of about 50° C. under said operating temperatures.

11. A solid electrolytic material according to claim 10, wherein said polymer material is neutral or charged with a majority of cationic sites, and is formed from a single type of polymer or copolymer, or contains a mixture of several polymers, copolymers or polymers and copolymers.

12. A solid electrolytic material according to claim 11, wherein said polymer material comprises polyalkyleneoxides, polyamides, polyphosphazenes or polyalkyleneimines.

13. A solid electrolytic material according to claim 12, wherein said polyalkyleneoxides comprise polypropylene oxides (POP) and polyethylene oxide (POE).

14. A solid electrolytic material according to claim 12, wherein said polyphosphazenes comprise ether groups of the formula:

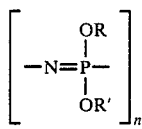

in which R and R' represent saturated hydrocarbon chains, or such chains substituted with one or several heteroatoms selected from O and N, and n is the number of repeating units in said polymer.

15. A solid electrolytic material according to claim 12, wherein said ppolyphosphazenes comprise groups bearing secondary amine, tertiary amine or quarternary ammonium functions, alone or in combination, and conform to the formula:

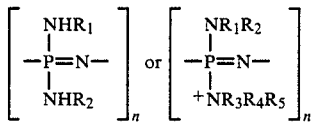

in which $R_1$ to $R_5$ represent saturated hydrocarbons chains, or such chains substituted with one or several heteroatoms selected from O and N, and n is the number of repeating units in said polymer.

16. A solid electrolytic material according to claim 12, wherein said polyamides comprise repeating units of the formula:

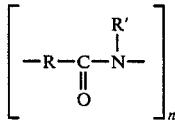

in which R and R' represent saturated hydrocarbon chains, or such chains substituted with one or several heteroatoms selected from O and N, and n is the number of repeating units in said polymer.

17. A solid electrolytic material according to claim 12, wherein said polyalkyleneimines comprise substituted polyethyleneimine repeating units of the formula:

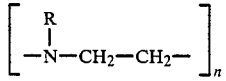

in which R represents a saturated hydrocarbon chain, or such chain substituted with one or several herteroatoms selected from 0 and N, and n is the number of repeating units in said polymer.

18. A solid electrolytic material according to claim 11, wherein said polymer material comprises perfluouroalkyl side chains.

19. A solid electrolytic material according to claim 11, wherein said polymer material comprises charged or uncharged binding sites permitting transitory solvation of $O_2{}^-$ ions.

20. A solid electrolytic material according to claim 19, wherein said binding sites are pyridyl groups or sulfonamide groups of the formula:

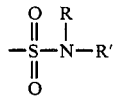

in which R and R' represent saturated hydrocarbon chains, or such chains substituted with one or several heteroatoms selected from O and N.

21. A solid electrolytic material according to claim 11, wherein siad polymer material comprises one or several anion-exchange resins comprising quaternary ammonium groups in repeating units selected from the formula:

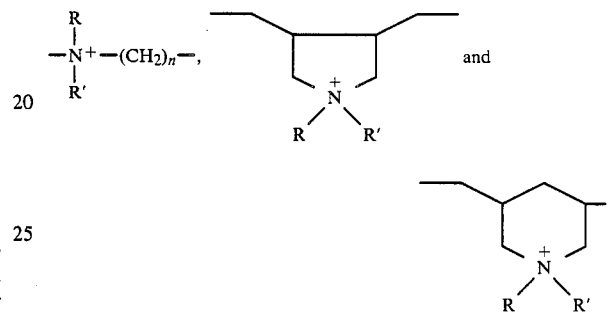

in which R and R' represents saturated hydrocarbon chains, or such chains substituted with one or several heteroatoms selected from O and N, and n is an integer of about 1 to 10, said resins initially having present therein anions chosen from $F^-$, $OH^-$, $I^-$, $B(Ph)_4{}^-$, $CO_3{}^{--}$ and $CH_3COO^-$, said anions having been exchanged, totally or partially, with $O_2{}^-$ anions.

22. A solid electrolytic material according to claim 21, wherein said resins is an ionic homo- or co-polymer derived from one or several vinylic or allylic quarternary ammonium monomers.

23. A solid electrolytic material according to claim 1, further comprising at least one additive capable of increasing the ionic conductivity of said matrix, said additive being chosen from polar plasticizing agents, organic salts and neutral additives comprising a pyridine nucleus.

24. A solid electrolytic material according to claim 22, wherein, said additives are 2,4,6-trimethoxybenzonitrile, 2,2'-bipyridine or quaternary ammonium slats $NR_4{}^+A^-$, in which R represents a saturated hydrocarbon chain, or such chain substituted with one or several heteroatoms selected from O and N, and $A^-$ is $ClO_4{}^-$, $B(C_6H_5)_4{}^-$, $PF_6{}^-$, or $C_nF_{2n+1}SO_3{}^-$ with n being an integer of about 1 to 10.

25. A solid electrolytic material according to claim 10, wherein said polymer material is reticulated or cross-linked.

26. A solid electrolytic material according to claim 10, wherein said polymer material is reticulated or cross-linked and comprises a weft formed from another polymer or copolymer that is inert with respect to $O_2{}^-$ ions.

27. A solid electrolytic material according to claim 10, wherein said polymer material comprises a weft formed from another polymer or copolymer that is inert with respect to $O_2{}^-$ ions.

28. A solid electrolytic material according to claim 1, wherein said liquid or gelled electrolyte is a concentrated superoxide salt solution or a superoxide molten salt.

29. A solid electrolytic material according to claim 1, wherein said porous support is formed from a material selected from glass, ceramic and polymer.

30. Process for preparation of solid electrolytic materials allowing oxygen transfer at a temperature not exceeding about 100° C., said materials comprising mobile superoxide anions $O_2^-$ incorporated in a matrix which is chemically stable with respect to said anions, this matrix being either based on a solid electrolytic macromolecular substance, or formed by the combination of a liquid or gelled electrolyte and a porous support, said support being based on glass, ceramic or polymer materials and said liquid electrolyte being a concentrated superoxide salt solution or a superoxide molten salt, said process comprising incorporating $O_2^-$ anions in a said matrix, this incorporation being effected by chemical means in the presence of an organic solvent in which said matrix and a superoxide salt are soluble or may be rendered soluble with the aid of additives, or by electrochemical means in which accumulation of $O_2^-$ ions is effected in an electrolytic said matrix by replacement of other electroactive anions pre-exisiting in the matrix, said pre-existing anions being eliminated by anodic oxidation in proportion to generation of $O_2^-$ ions at a cathode subjected to a flow of gaseous or dissolved oxygen.

31. Process according to claim 20, and preparing the superoxide-containing electrolytic materials in the form of a membrane, by evaporating said solvent from a mixture comprising a first solution of said matrix, and a second solution of the superoxide salt, these solutions being degasified, and the resultant membrane being dried under a current of inert gas at a controlled temperature followed by an annealing at a temperature near the fusion of the matrix material, so long as the superoxide is not degraded at this temperature.

32. Process for preparation of quarternary ammonium superoxides suitable for use in the process according to claim 30, comprisinf reacting in an organic solvent medium selected from pyridine, DMSO, DMF and acetonitrile the following reactants:
a quaternary ammonium salt having an anion inert with respect to $O_2^-$ chosen from $F^-$, $I^-$, $OH^-$, $NO_3^-$, $ClO_4^-$, $CH_3COO^-$ and $CO_3^{--}$; and
an excess of superoxide salt having a cation selected from $Na^+$, $K^+$, $Rb^+$, $Cs^+$ or tetramethylammonium.

33. A solid electrolytic material according to claim 1, further comprising electronically conducting particles incorporated in said matrix, these particles being in a concentration sufficient to confer to said material an electronic conductivity at said operating temperatures.

34. A solid electrolytic material according to claim 33, wherein said matrix is a polymeric material and the conducting particles are carbon or magnetite $Fe_3O_4$.

35. A solid electrolytic material according to claim 34, wherein said polymeric material of the matrix is a polyalkylene oxide comprising polypropylene oxide (POP) or polyethylene oxide (POE) groups, or POP and POE groups.

36. A solid electrolytic material according to claim 13, comprising a statistical copolymer having ethylene oxide and propylene oxide units, said propylene oxide units being present in a molar concentration between 5% and 40%, the molecular weight of the copolymer being on the order of 5,000 to 500,000.

37. A solid electrolytic material according to claim 23, in the form of a membrane comprising a mixture of polymers/additive/superoxide according to a weight ratio of about 6/1/2, the mixture of polymers comprising polyethylene oxide and polypropylene oxide according to a weight ratio of about 4/2.

38. A solid electrolytic material according to claim 37, wherein said membrane comprises polyethyleneoxide/polypropylene-oxide/tetrahexylammonium perchlorate/tetrabutylammonium superoxide, according to a weight ratio of about 3 to 5/2/1/2, or polyethyleneoxide/polypropylene-oxide/tetrahexylammonium perchlorate/$KO_2$/crown ether 18-crown-6 according to a weight ratio of about 3 to 5/2/1/0.4/0.4.

39. An electrochemical cell for oxygen transfer employing $O_2^-$ ions as selective transporters of oxygen and current, comprising a matrix of a solid electrolytic material according to claim 1, through which said ions are displaced.

40. An electrochemical cell according to claim 39, wherein said electrolytic material is in the form of a membrane compressed between two coextensive electrodes face to face with the said membrane, these electrodes being constituted by a conducting material permeable to oxygen gas, inert with respect to the electrolytic material at a temperature less than 100° C. and unoxidizable at least at the anode, this material being identical or different for the two electrodes.

41. An electrochemical cell according to claim 40, wherein said electrode materials comprise carbon.

42. An electrochemical cell according to claim 40, wherein at least one of the electrodes is formed from the combination of a weft of a polymer having high properties of resistance, supporting a very thin film of electronically conducting polymer itself charged with glassy carbon powder or another product assuring a good electronic transfer, or also one or several materials conferring to it properties of both electronic and ionic conduction with respect to $O_2^-$ ions.

43. An electrochemical cell according to claim 40, further comprising a mixed electronic and ionic conductor, interposed between the electrode and the electrolyte, in which $O_2$ is soluble.

44. An electrochemical cell according to claim 40, in the form of small modules in each of which said membrane has a working area of several tens to several hundreds of $m^2$, said modules being either cylindrical with a spirally wound membrane, or comprising said membranes folded accordion style in a container, said modules being mounted in series, in parallel or in parallel series.

45. Process for selective transfer of oxygen from a first medium to a second medium, said process comprising the following successive steps:
electrochemically reducing oxygen from said first medium leading to transitory formation of $O_2^-$ ions;
diffusing oxygen in the $O_2^-$ form through an electrolytic material allowing superoxide ion transfer at a temperature not exceeding about 100° C., said material comprising mobile superoxide anions $O_2^-$ incorporated in a matrix which is chemically stable with respect to said anions, this matrix being based on a solid electrolytic macromolecular material, or formed by the combination of a liquid or gelled electrolyte and a porous support, said support being based on glass, ceramic or polymer materials and said liquid electrolyte being a concentrated superoxide salt solution or a superoxide molten salt, said material constituting an essentially completely gas-impermeable barrier; and oxidizing the $O_2^-$ ions to oxygen in said second medium.

46. Process according to claim 44, comprising employing an electrochemical cell which contains said electrolytic material in the form of a membrane compressed between two coextensive electrodes permeable to gases and face to face with said membrane, said cell separating the first and second media, said electrodes having respective terminals, and imposing an electric potential difference with the aid of an exterior electric generator to said terminals.

47. Process according to claim 44, comprising employing an electrochemical cell which contains said electrolytic material in the form of a membrane compressed between two coextensive electrodes permeable to gases and face to face with said membrane, said cell separating said first and said second media, said electrodes having respective terminals, said two terminals being connected via an exterior circuit devoid of means for applying electric potential and comprising a switch and a variable resistance system, which permits regulating or interrupting the flow of oxygen transferred from the medium at higher partial pressure of oxygen to the medium at lower partial pressure, a difference of oxygen partial pressure being maintained between the two media.

48. Process for selective transfer of oxygen from a first gaseous medium at a first partial pressure of oxygen, towards a second medium at a second, lower partial pressure of oxygen, comprising maintaining a difference of oxygen partial pressure between the said media separated by a membrane comprising a material according to claim 33.

49. Process for measuring the partial pressure of oxygen in a gas, comprising measuring a difference of electric potential appearing at the terminals of the electrodes of an electrochemical cell according to claim 38 separating two media, while maintaining a reference partial pressure of oxygen in a first medium adjacent one electrode and admitting a gas at a partial pressure of oxygen to be measured in the second medium adjacent the other electrode.

50. Process for selective transfer of oxygen from a first gaseous medium at a high partial pressure of oxygen, comprising maintaining a difference of oxygen partial pressure between the media under consideration, separated by an electrochemical cell according to claim 40, and using as a source of electric energy the electric voltage generated at the terminals of the electrodes.

* * * * *